United States Patent [19]
Wickham

[11] Patent Number: 5,492,128
[45] Date of Patent: Feb. 20, 1996

[54] INTRACARDIAC ELECTROGRAM SENSING IN AN ARRHYTHMIA CONTROL SYSTEM

[75] Inventor: John Wickham, Fivedock, Australia

[73] Assignee: Telectronics Pacing Systems, Inc., Englewood, Colo.

[21] Appl. No.: 328,695

[22] Filed: Oct. 25, 1994

Related U.S. Application Data

[62] Division of Ser. No. 901,644, Jun. 22, 1992, Pat. No. 5,395,393.

[30] Foreign Application Priority Data

Nov. 1, 1991 [AU] Australia ................... PK9242

[51] Int. Cl.$^6$ ..................................................... A61B 5/04
[52] U.S. Cl. ............................................................. 128/696
[58] Field of Search ........................... 607/4, 5; 128/695, 128/696, 700, 702–705

[56] References Cited

U.S. PATENT DOCUMENTS

| | | |
|---|---|---|
| 4,184,493 | 1/1980 | Langer . |
| 4,440,172 | 4/1984 | Langer . |
| 4,903,699 | 2/1990 | Baker, Jr. . |
| 4,913,146 | 4/1990 | DeCole, Jr. ................ 128/696 |
| 4,940,052 | 7/1990 | Mann . |
| 4,940,054 | 7/1990 | Grevis . |
| 5,010,887 | 4/1991 | Thornander ............... 128/696 |
| 5,048,521 | 9/1991 | Pless . |
| 5,083,563 | 1/1992 | Collins . |
| 5,111,815 | 5/1992 | Mower . |
| 5,111,816 | 5/1992 | Pless . |
| 5,144,947 | 8/1992 | Wilson . |
| 5,159,926 | 11/1992 | Ljungstroem . |
| 5,188,116 | 2/1993 | Pommrehn et al. ............. 128/696 |
| 5,357,969 | 10/1994 | Herleikson ................. 128/696 |

Primary Examiner—William E. Kamm
Attorney, Agent, or Firm—Gottlieb Rackman & Reisman

[57] ABSTRACT

An implantable cardioverter/defibrillator device having an improved sensing system for automatically and rapidly adjusting to changing amplitudes of intracardiac electrogram "ICEG" signals during transitions between normal sinus rhythm and ventricular tachycardia/ventricular fibrillation of a patient's heart is disclosed. ICEG signals are sensed, amplified and filtered to remove high frequency and low frequency noise and artifacts therefrom. Crossings of positive and negative threshold levels by the filtered signals are detected and corresponding positive and negative output signals representative thereof are provided. The positive and negative threshold levels are varied in accordance with corresponding variations of fractions of the levels of the filtered signals so that the positive and negative threshold levels move independently of one another in response to changes in the levels of the filtered signals; and, the positive and negative output signals generated during each heart beat are rationalized so that only one output signal is provided per heart beat.

24 Claims, 5 Drawing Sheets

INTRACARDIAC ELECTROGRAM SENSING IN AN ARRHYTHMIA CONTROL SYSTEM

This is a divisional of application Ser. No. 07/901,644 filed on Jun. 22, 1992 and now U.S. Pat. No. 5,395,393.

FIELD OF THE INVENTION

This invention relates to implantable cardioverter/defibrillator (ICD) devices that automatically detect dangerous heart arrhythmias and provide appropriate therapy to restore normal sinus rhythm (NSR) and, more particularly, to improvements in the sensing systems thereof which sense the heart's electrical activity.

BACKGROUND OF THE INVENTION

As used herein, the term "arrhythmia" refers to any abnormal heart rhythm that may be dangerous to the patient and specifically includes fibrillation, tachycardias, supraventricular tachycardias (SVT), ventricular tachycardias (VT), ventricular fibrillation and flutter (VF) and bradycardia. As further used herein, the term "therapy" refers to any means used by the ICD device to restore normal heart rhythm, such as defibrillation, cardioversion, antitachycardia pacing and drug infusion. The disclosed invention has application to ICD devices which treat tachyarrhythmias (abnormally high heart rate) and/or bradyarrhythmias (low heart rate).

Modern conventional bradycardia pacemakers all have sensing mechanisms to enable the device to inhibit pacing when the heart is beating normally. Implantable tachyarrhythmia devices must also sense the heart's electrical activity, known as the intracardiac electrogram (ICEG), to determine whether the patient needs treatment. Intracardiac electrograms exhibit highly variable amplitudes during transitions from normal sinus rhythm to rhythms such as ventricular tachycardia and ventricular fibrillation. Because of this, it is advantageous that such sensing systems have the ability to automatically adjust to the changing amplitude of the signal.

U.S. Pat. No. 4,184,493 to Langer et al., which issued on Jan. 22, 1980, and is entitled "Circuit for Monitoring a Heart and for Effecting Cardioversion of a Needy Heart" describes such a sensing circuit that automatically adjusts to the amplitude of the heart's electrical signal using a conventional feedback automatic gain system. One problem with this form of automatic sensing is that its response time is slow, due to the damping required to maintain stability of the feedback loop.

Another form of automatic sensing system is described in U.S. Pat. No. 4,903,699 to Baker et al., which issued on Feb. 27, 1990, and is entitled "Implantable Cardiac Stimulator With Automatic Gain Control". The Baker et al. patent uses a system of comparators and adjustable thresholds to optimally detect the ICEG signal. As in the case of the above Langer et al. patent, the response time of this system is slow, thereby resulting in a reduction of speed and efficiency of the sensing system.

Both of the foregoing patents describe systems which filter the ICEG signal to remove low frequency noise and artifacts. High pass filtering is also required to prevent sensing of T-Waves during normal sinus rhythm (NSR). A problem with these techniques is that the high pass filtering attenuates the signal during VF, since the VF signal is often likely to have a spectral content similar to that of T-Waves.

It is, therefore, a primary object of this invention to provide an improved cardiac signal detection system having a fast response to a patient's electrical cardiac activity in rhythms such as NSR, SVT, VT and VF.

It is a further object of this invention to provide reliable sensing of cardiac activity when the amplitude of the ICEG signal is varying rapidly.

It is another object of this invention to sense only the QRS complex of the ICEG during normal sinus rhythm of the heart, without sensing T-Waves, in order to prevent VF attenuation.

It is a still further object of the invention to provide a method and apparatus for optimally sensing the intracardiac electrogram with an implantable antiarrhythmia device that provides optimum sensing with different levels of input signals and different signal morphologies while being immune to false sensing of T-Waves and other artifacts.

Further objects and advantages of this invention will become apparent as the following description proceeds.

SUMMARY OF THE INVENTION

Briefly stated, and in accordance with one embodiment of the invention, an arrhythmia control system is provided having an amplifier that is connected to intracardiac sensing and pacing electrodes in order to sense the ICEG. The output of the amplifier is connected to a filter which removes high frequency and low frequency noise and artifacts. The output of the filter is passed to a dual dynamic threshold detector, which produces first and second digital "Raw_Sense" outputs. The first digital Raw_Sense output is produced when the signal crosses a positive threshold and the second digital Raw_Sense output is produced when the signal crosses a negative threshold. The two thresholds are independent and dynamic, being derived from a fraction of the positive or negative portions of the filtered signal. Also, the ranges of the thresholds are limited, there being an upper threshold range limit of approximately 5 mV of input voltage for each threshold to prevent transients from unduly influencing the thresholds, and a lower threshold range limit of approximately 0.2 mV of input voltage for each threshold to prevent their sensing of electronic noise during the absence of any cardiac activity.

According to a further aspect of the invention, the first and second digital Raw-Sense outputs are combined with an event clustering algorithm, which reduces the numerous raw detections to one "Valid_Sense" output per heart beat from the clustering algorithm. A separate second output is provided by the clustering algorithm that indicates when the input signal has been contaminated with interference.

In a preferred embodiment, the filter for removing high and low frequency noise and artifacts consists of a first order high pass filter with a corner frequency of 2 Hz, followed by a second order band pass filter of 25 Hz with a Quality factor of 1.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
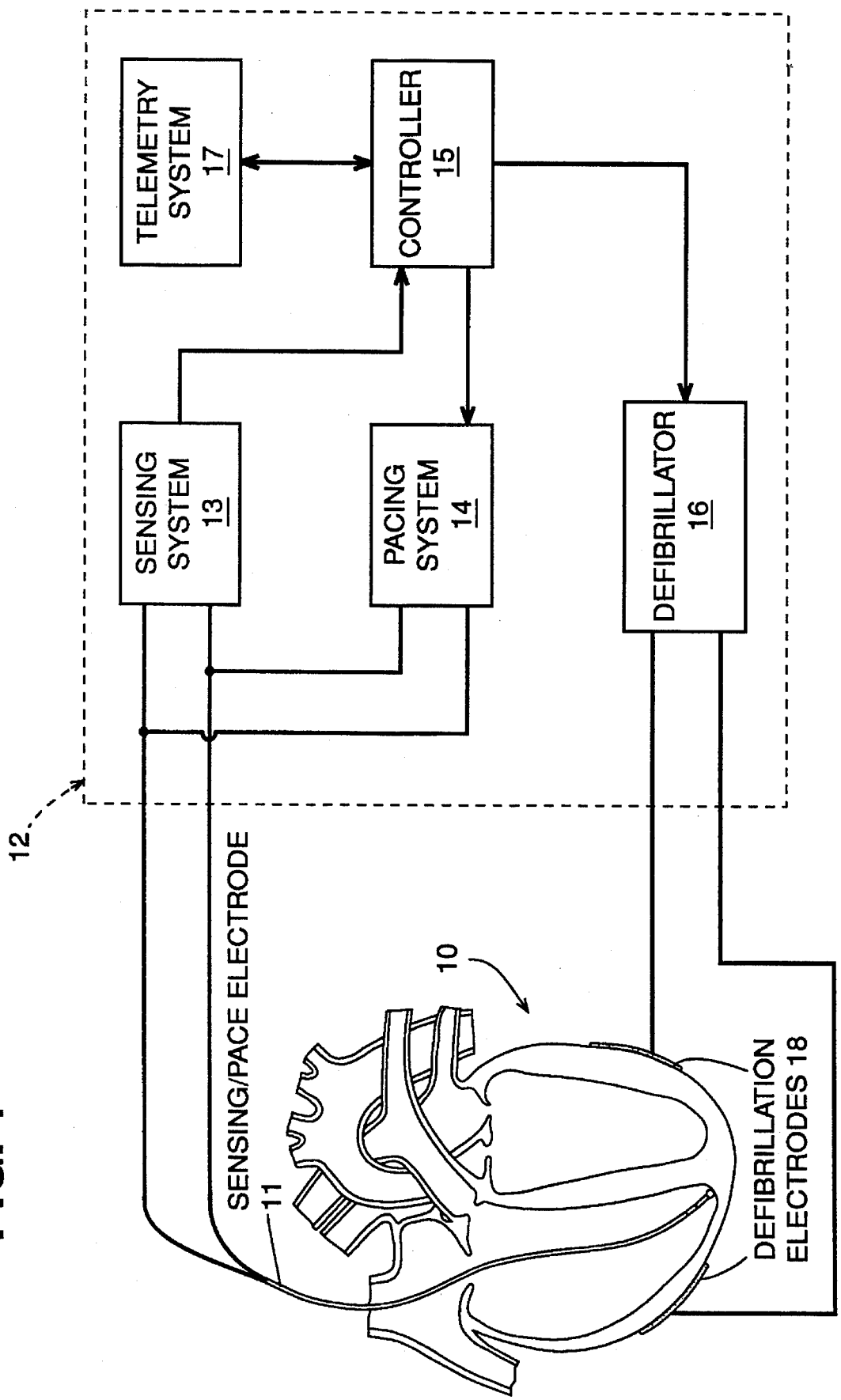
FIG. 1 is a block diagram of an arrhythmia control system in accordance with the present invention.

Referring to FIG. 1, there is depicted a block diagram of an arrhythmia control system which includes an ICD device 12 and a cardiac sense/pace lead 11 that is connected to the patient's heart 10. The intracardiac electrogram signal (ICEG) from lead 11 is processed by a sensing system 13 to identify valid cardiac contractions. A controller 15 analyzes the time sequence of these detections and automatically determines whether the patient's heart is in arrhythmia. If so, it selects an appropriate therapy. For therapy, the controller can cause conventional cardiac pacing pulses to be delivered to the heart from a pacing system 14 via the sense/pace leads 11, or it can cause a cardioversion or defibrillation shock to be delivered via a defibrillator system 16 and defibrillation electrodes 18. The ICD device 12 can be interrogated and adjusted by radio via a telemetry system 17.

Figure 2:
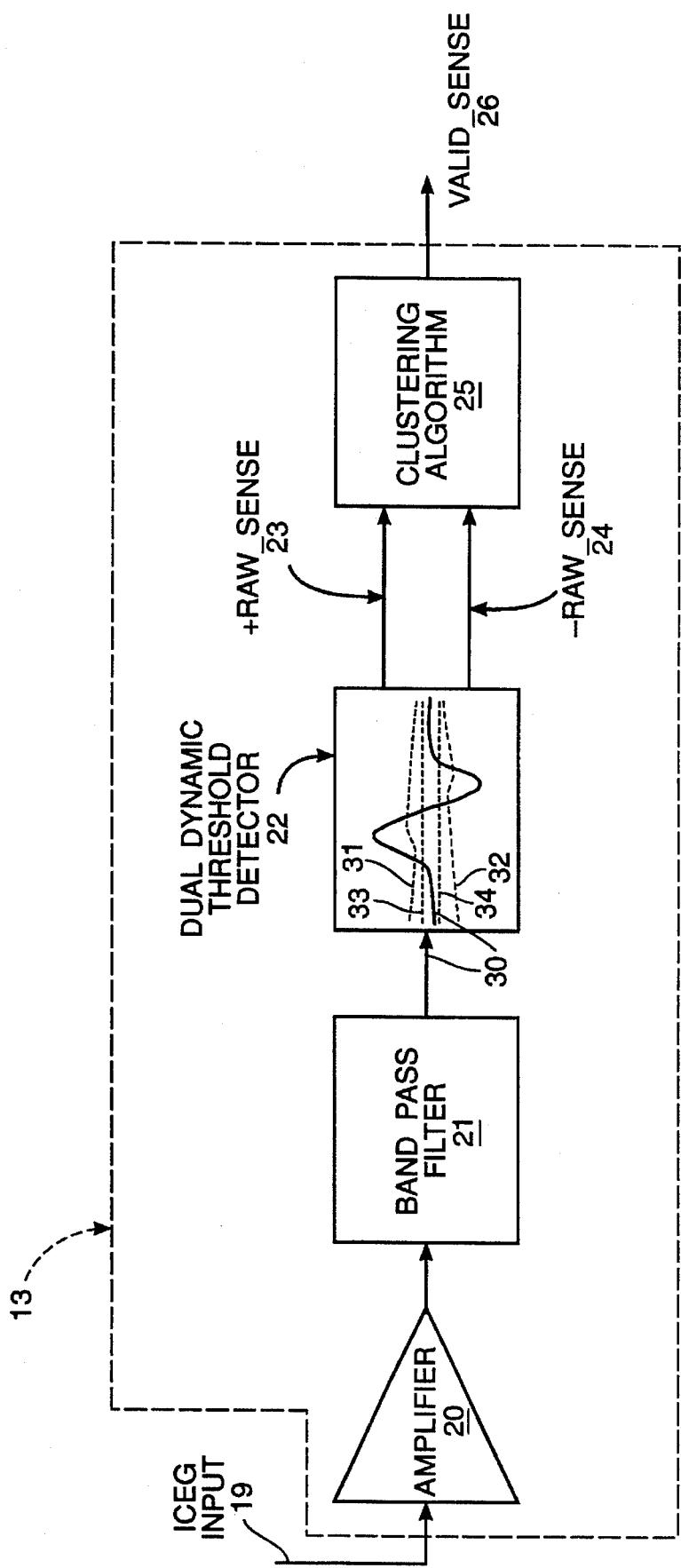
FIG. 2 is a block diagram of a sensing system shown in FIG. 1.

Referring to FIG. 2, there is depicted a block diagram of the sensing system 13 of FIG. 1. Sensing system 13 comprises an amplifier 20 which amplifies ICEG input 19 to an appropriate level for the subsequent stages of processing. The amplified signal output of amplifier 20 is then passed through a band pass filter 21 to remove high and low frequency noise and artifacts from it. The filtered signal output 30 from filter 21, in turn, is passed to a dual dynamic threshold detector 22. This detector generates two independent voltage thresholds, a positive threshold 31 and a negative threshold 32, and produces a digital "+Raw_Sense" 23 output when the signal is greater than the positive threshold, and a "−Raw_Sense" 24 output when the signal is less than the negative threshold.

The +Raw_Sense 23 and −Raw_Sense 24 output signals are passed to a clustering algorithm 25 for rationalization. Typically, each QRS complex in the ICEG will produce between 2 and 10 raw detects. The clustering algorithm 25 reduces these to one digital output per heart beat, which output is identified as Valid_Sense 26 in FIG. 2.

Figure 3:
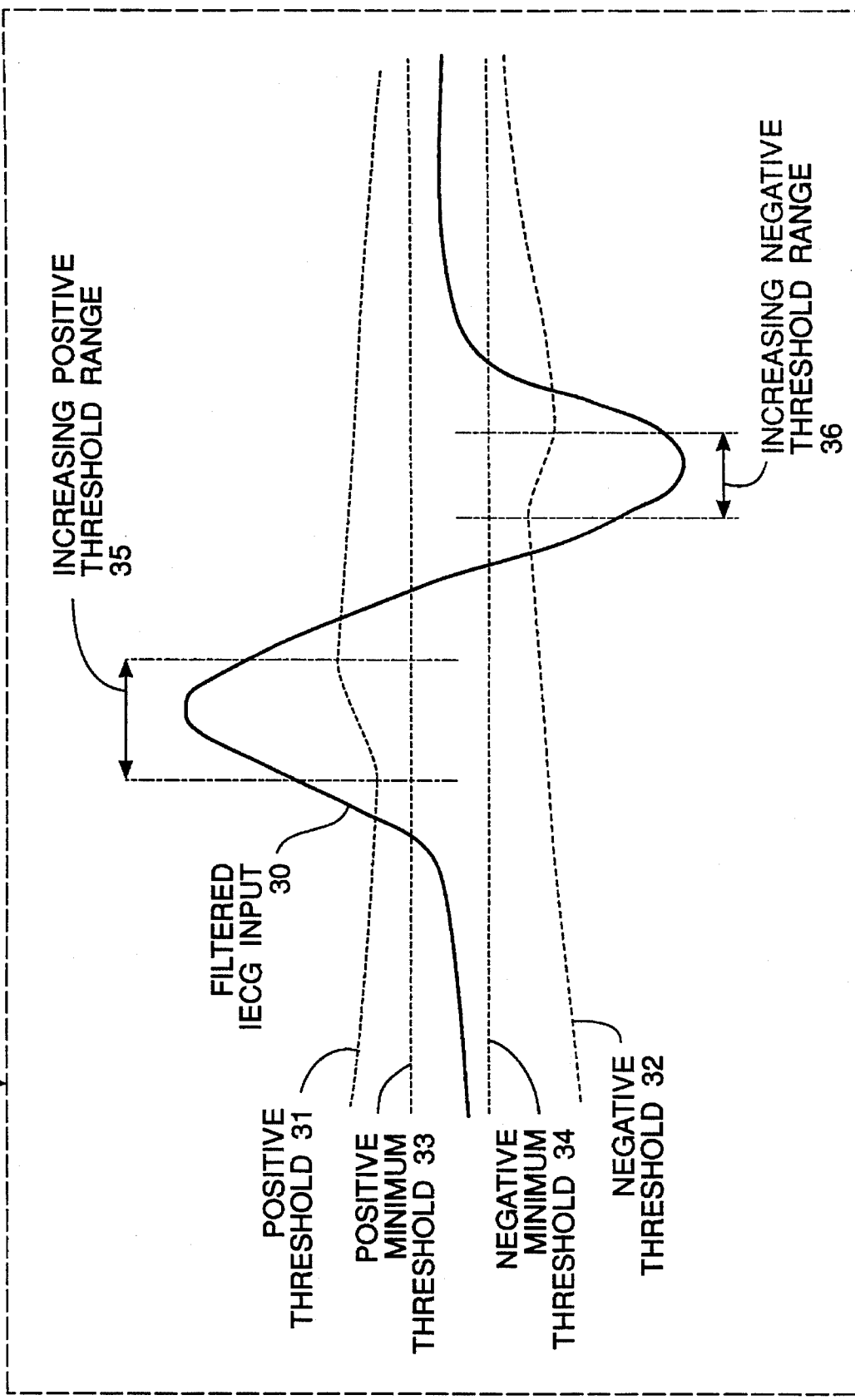
FIG. 3 details the behavior of two dynamic thresholds employed in the sensing system of FIGS. 1 and 2.

Referring to FIG. 3, the operation of the dual dynamic threshold detector of FIG. 2 is there depicted. When the positive threshold 31 is greater than one-half of the filtered ICEG input signal 30, the positive threshold decays exponentially towards a positive minimum threshold 33 with a time constant of approx 0.75 seconds. Positive minimum threshold 33 limits the level to which the positive threshold can decay to approximately 0.2 mV. When the positive threshold 31 is less than one-half of the input signal 30, as shown by the range 35, the positive threshold increases toward one-half of the input signal, with a shorter time constant of 0.05 secs. A "+Raw_Sense" digital output is generated whenever the input signal 30 exceeds the positive threshold 31.

The operation of the negative threshold 32 vis-a-vis a negative minimum threshold 34 is a polarity mirror image of that of the positive threshold 31, and includes a range 36 that corresponds to the range 35 thereof.

Both thresholds have upper limits in that the positive threshold 31 cannot exceed a maximum value (in the preferred embodiment this is 10 to 30 times the minimum threshold), nor can the negative threshold 32 exceed a corresponding negative maximum value.

Figure 4:
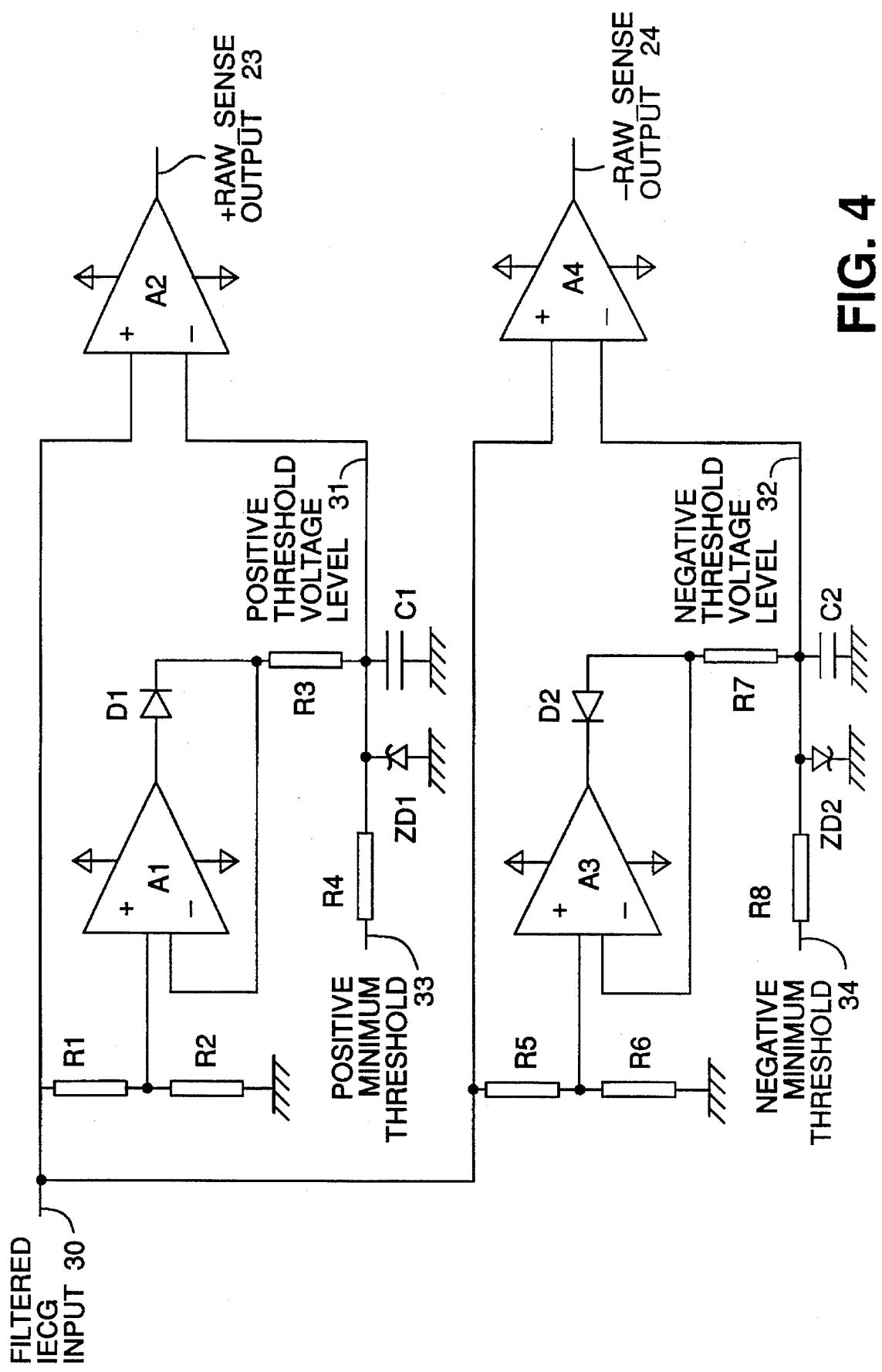
FIG. 4 illustrates a circuit for generating the two dynamic thresholds of FIG. 3; and, FIG. 5 is a state transition diagram for the clustering algorithm.

Referring to FIG. 4, there is depicted a circuit for implementing the function of dual dynamic threshold detector 22. The positive threshold 31 of FIG. 3 is stored as a voltage on capacitor C1. When the filtered ICEG input 30 exceeds this voltage, the output of amplifier A2 goes high to output a +Raw_Sense signal 23. When one-half of the input voltage 30 is less than the positive threshold value on capacitor C1, the voltage on capacitor C1 discharges exponentially through a resistor R4 towards the positive minimum threshold 33, which sets the minimum threshold voltage level. Resistors R1 and R2 provide one-half of the input voltage 30 to a precision rectifier formed by amplifier A1 and diode D1. When one-half of the input voltage exceeds the voltage on capacitor C1, the capacitor is charged up to this value through resistor R3, with a time constant of 0.05 secs. A Zener diode ZD1 limits the maximum charge on capacitor C1 to an equivalent of approximately 5 mV at the input.

A −Raw_Sense output 24 with respect to negative threshold 32 of FIG. 3 is provided by a polarity mirror image of the above circuit, employing amplifiers A3 and A4 and corresponding associated components R5–R8, D2, C2 and ZD2.

Figure 5:
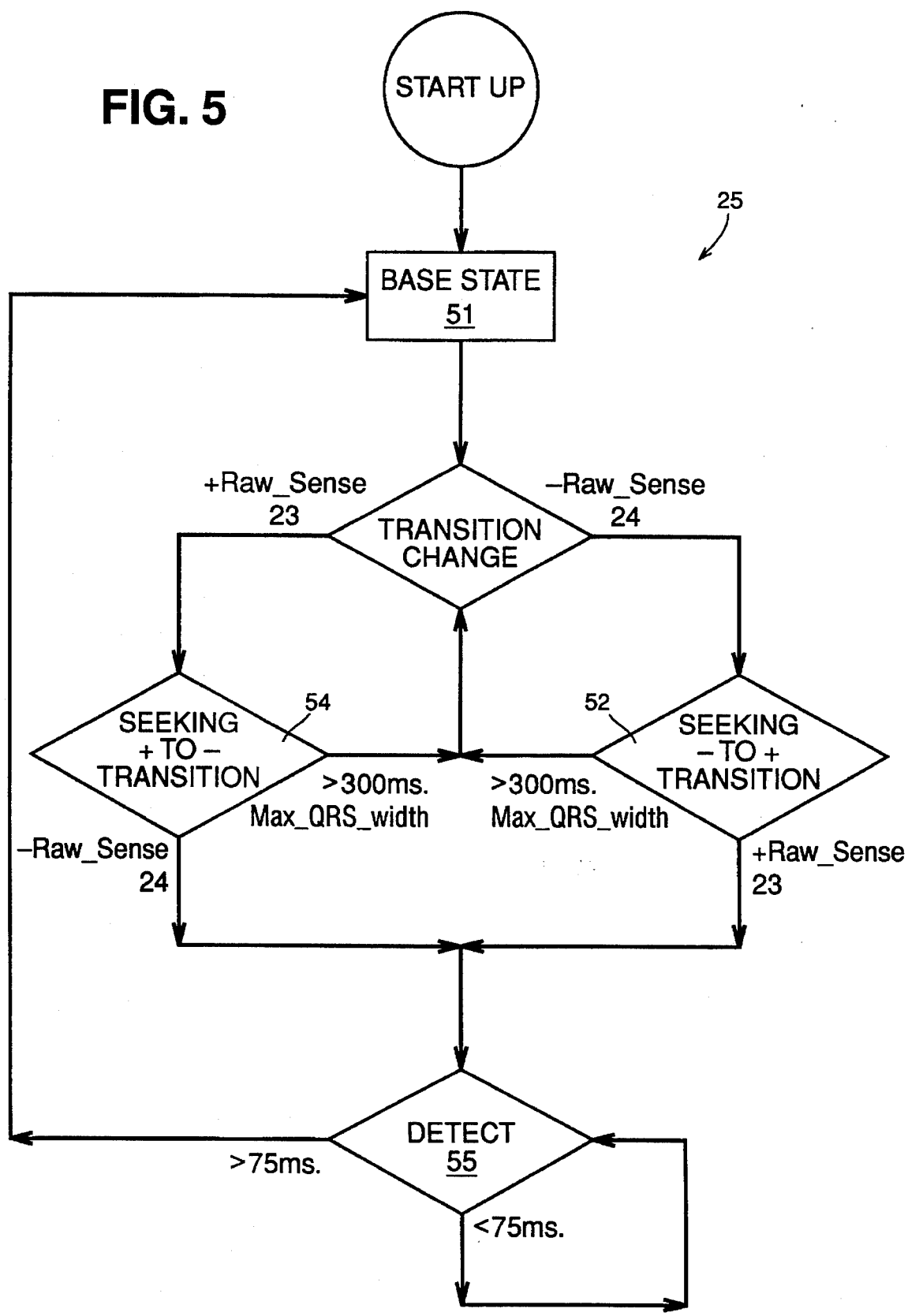

Referring to FIG. 5, the operation of the clustering algorithm 25 of FIG. 2 is there depicted in a state transition diagram format. On start up, the algorithm commences operation in a base state 51. If a −Raw_Sense input 24 is received from the dual threshold comparator 22 (FIG. 4), the algorithm changes to a "seeking − to + transition" state 52. If a +Raw_Sense input 23 is received instead, the algorithm changes from the base state 51 to a "seeking + to − transition" state 54. If the algorithm spends more than 300 ms in either the seeking − to + transition state 52 or the seeking to − transition state 54, the algorithm reverts back to the base state 51. The 300 ms limit represents a selectable maximum anticipated width of a QRS complex If while the algorithm is in the seeking − to + transition state 52 a +Raw_Sense input 23 is received, the algorithm changes to the "detect!" state 55 and, at this point, a Valid_Sense output 26 is issued. Similarly, if while the algorithm is in the seeking + to − transition state 54 a −Raw_Sense input 24 is received, the algorithm also changes to the "detect!" state 55. In either case the algorithm remains in the detect!" state for 75 ms and then reverts back to the base state 51 to await the arrival of the next triggering input signal.

The main feature of clustering algorithm 25 is that it generates Valid_Sense outputs 26 whenever transitions are triggered from the base state to one threshold and then to the other threshold within a time window, which is programmed at 300 ms in the preferred embodiment.

The clustering algorithm 25 can be implemented either by discrete electronic logic, or as a computer program that can be part of the controller 15 for the implantable defibrillator 16 of FIG. 1.

It will be apparent from the foregoing description that the present invention provides an improved cardiac signal detection system that responds rapidly to a patient's electrical cardiac activity in rhythms such as NSR, SVT, VT and VF and provides reliable sensing of such activity even when the amplitude of the ICEG signal is varying rapidly. In addition, it will be apparent that the invention provides an improved apparatus and method for optimally sensing the intracardiac electrogram with an implantable antiarrhythmia device that provides optimum sensing with different levels of input signals and different signal morphologies, while being immune to false sensing of T-waves and other artifacts. Further, the invention senses only the QRS complex of the ICEG during normal sinus rhythm of the heart, without sensing T-waves, in order to prevent VF attenuation.

While there has been shown and described what is presently considered to be the preferred embodiment of this invention, it will be obvious to those skilled in the art that various changes and modifications may be made without departing from the broader aspects of this invention. It is, therefore, aimed in the appended claims to cover all such changes and modifications as fall within the true spirit and scope of this invention.

What is claimed is:

1. A method for automatically and rapidly adjusting to changing amplitudes of intracardiac electrogram "ICEG" signals received by an implantable cardioverter/defibrillator during transitions between normal sinus rhythm and ventricular tachycardia/ventricular fibrillation of a patient's heart, comprising the steps of:

sensing and amplifying said ICEG signals;

filtering said amplified ICEG signals to remove high frequency and low frequency noise and artifacts therefrom;

detecting when levels of said filtered signals cross positive and negative threshold levels and providing corresponding positive and negative output signals representative thereof; and varying said positive and negative threshold levels in accordance with corresponding variations of fractions of the levels of said filtered signals, whereby said positive and negative threshold levels move independently of one another in response to changes in the levels of said filtered signals.

2. A method according to claim 1, including the further step of causing said positive threshold level to decay toward a positive minimum threshold level when said positive threshold level is greater than one-half of the level of said filtered signal.

3. A method according to claim 2, including the further step of causing said positive threshold level to increase toward one-half of the level of said filtered signal when said positive threshold level is less than one-half of the level of said filtered signal.

4. A method according to claim 3, including the further step of limiting said increase in said positive threshold level to a predetermined maximum positive value.

5. A method according to claim 3, including the further step of limiting said increase in said positive threshold level to a predetermined maximum positive value in the range of ten to thirty times the value of said positive minimum threshold level.

6. A method according to claim 1, including the further step of causing said negative threshold level to decrease toward a negative minimum threshold level when said negative threshold level exceeds one-half of the negative level of said filtered signal.

7. A method according to claim 1, including the further step of causing said negative threshold level to increase toward one-half of the negative level of said filtered signal when said negative threshold level is less than one-half of the negative level of said filtered signal.

8. A method according to claim 7, including the further step of limiting said increase in said negative threshold level to a predetermined maximum negative value.

9. A method according to claim 7, including the further step of limiting said increase in said negative threshold level to a predetermined maximum negative value in a range of ten to thirty times the value of said negative minimum threshold level.

10. A method for automatically and rapidly adjusting to changing amplitudes of intracardiac electrogram "ICEG" signals received by an implantable cardioverter/defibrillator device during transitions between normal sinus and ventricular tachycardia/ventricular fibrillation of a patient's heart, comprising the steps of:

sensing and amplifying said ICEG signals;

filtering said amplified ICEG signals to remove high frequency and low frequency noise and artifacts therefrom;

detecting when levels of said filtered signals cross positive and negative threshold levels and providing a plurality of corresponding positive and negative output signals during each heart beat representative thereof;

rationalizing said plurality of output signals so as to provide only one output signal per heart beat; and varying said positive and negative threshold levels in accordance with corresponding variations of fractions of the levels of the said filtered signals, whereby said positive and negative threshold levels move independently of one another in response to changes in the levels of said filtered signals.

11. A method according to claim 10, including the further step of causing said positive threshold level to decay toward a positive minimum threshold level when said positive threshold level is greater than one-half of the level of said filtered signal.

12. A method according to claim 10, including the further step of causing said positive threshold level to increase toward one-half of the level of said filtered signal when said positive threshold level is than one-half of the level of said filtered signal.

13. A method according to claim 12, including the further step of limiting said increase in said positive threshold level to a predetermined maximum positive value.

14. A method according to claim 12, including the further step of limiting said increase in said positive threshold level to a predetermined maximum positive value in a range of ten to thirty times the value of said positive minimum threshold level.

15. A method according to claim 10, including the further step of causing said negative threshold level to decrease toward a negative minimum threshold level when said negative threshold level exceeds one-half of the negative level of said filtered signal.

16. A method according to claim 10, including the further step of causing said negative threshold level to increase toward one-half of the negative level of said filtered signal when said negative threshold level is less than one-half of the negative level of said filtered signal.

17. A method according to claim 16, including the further step of limiting said increase in said negative threshold level to a predetermined maximum negative value.

18. A method according to claim 16, including the further step of limiting said increase in said negative threshold level to a predetermined maximum negative value in a range of ten to thirty times the value of said negative minimum threshold level.

19. A method according to claim 10, wherein said rationalizing step employs a clustering algorithm having a "base" state, a "seeking minus to plus transition" state, a "seeking plus to minus transition" state and a "detect" state, said rationalizing step including the substeps of commencing operation of said algorithm in said base state, switching to said seeking plus to minus transition state upon receipt of a positive output signal during said detecting step, and then switching to said detecting state and providing said one output signal in an event that a negative output signal is received during said detecting step within a predetermined time following the receipt of said positive output signal.

20. A method according to claim 19, wherein said rationalizing step includes the further sub-step of switching from said seeking plus to minus transition state back to said base state instead of to said detect state in an event said negative output signal is not received within said predetermined time.

21. A method according to claim 19, wherein said rationalizing step includes the further sub-step of switching from said detect state back to said base state at a second predetermined time following a receipt of said negative output signal.

22. A method according to claim 10, wherein said rationalizing step employs a clustering algorithm having a "base" state a "seeking minus to plus transition" state, a "seeking plus to minus transition" state and a "detect" state, said rationalizing step including the substeps of commencing operation of said algorithm in said base state, switching to said seeking minus to plus transition state upon receipt of a negative output signal during said detecting step, and then switching to said detect state and providing said one output signal in the event that a positive output signal is received during said detecting step within a predetermined time following the receipt of said negative output signal.

23. A method according to claim 22, wherein said rationalizing step includes the further substep of switching from said seeking minus to plus transition state back to said base state instead of to said detect state in the event said positive output signal is not received within said predetermined time.

24. A method according to claim 22, wherein said rationalizing step includes the further step of switching from said detect state back to said base state at a second predetermined time following a receipt of said positive output signal.

* * * * *